(12) United States Patent
Miller

(10) Patent No.: US 10,245,132 B2
(45) Date of Patent: Apr. 2, 2019

(54) MARKER CAPSULE FOR DRUG DELIVERY DART

(71) Applicant: Kevin G. Miller, Alvarado, TX (US)

(72) Inventor: Kevin G. Miller, Alvarado, TX (US)

(73) Assignee: Dart Markers, LLC, Alvarado, TX (US)

(*) Notice: Subject to any disclaimer, the term of this patent is extended or adjusted under 35 U.S.C. 154(b) by 0 days.

(21) Appl. No.: 15/446,095

(22) Filed: Mar. 1, 2017

(65) Prior Publication Data

US 2018/0250110 A1  Sep. 6, 2018

(51) Int. Cl.
*A61D 7/00* (2006.01)
*A61M 5/20* (2006.01)
*A61M 5/24* (2006.01)
*A01K 11/00* (2006.01)

(52) U.S. Cl.
CPC .............. *A61D 7/00* (2013.01); *A01K 11/005* (2013.01); *A61M 5/2053* (2013.01); *A61M 5/2459* (2013.01); *A61M 2005/2013* (2013.01)

(58) Field of Classification Search
CPC ..... A61D 7/00; A01K 11/005; A61M 5/2053; A61M 5/2459; A61M 2005/2013
See application file for complete search history.

(56) References Cited

U.S. PATENT DOCUMENTS

| | | | |
|---|---|---|---|
| 2,617,359 A | * | 11/1952 | Van Horn ............. A61M 5/282 102/512 |
| 3,037,454 A | | 6/1962 | Young |
| 3,701,533 A | | 10/1972 | Palmer |
| 3,861,943 A | | 1/1975 | Grainger |
| 4,656,092 A | | 4/1987 | Haman et al. |
| 5,001,880 A | | 3/1991 | Smith |
| 5,121,692 A | | 6/1992 | DiCarlo |
| 5,254,379 A | | 10/1993 | Kotsiopoulos et al. |
| 5,353,712 A | | 10/1994 | Olson |
| 5,654,524 A | * | 8/1997 | Saxby ..................... F42B 12/40 102/502 |
| 6,378,439 B1 | | 4/2002 | Saxby |
| 6,482,187 B1 | | 11/2002 | Gibbs |
| 6,513,439 B2 | | 2/2003 | Brown et al. |
| 6,736,070 B2 | | 5/2004 | Baltos |
| 7,013,810 B1 | | 3/2006 | Brydges-Price |
| 7,743,708 B1 | | 6/2010 | Lawrence |
| 7,882,786 B2 | | 2/2011 | DeHaan et al. |
| 9,234,729 B2 | | 1/2016 | Soars |
| 9,261,338 B2 | | 2/2016 | Saxby |

(Continued)

OTHER PUBLICATIONS

Pneu-Dart, Inc. PDF brochure for "Injection Marking Darts", file name: InjectionMarkingDart2015Web2.pdf.

*Primary Examiner* — Lauren P Farrar
(74) *Attorney, Agent, or Firm* — Dan Brown Law Office; Daniel R. Brown

(57) ABSTRACT

A marker capsule for a drug delivery dart that marks a animal upon impact to indicate it has had a drug injection. The marker capsule is formed of a rupturable material, and has a central aperture formed therethrough for disposition about a cannula extending from the drug delivery dart. A marking substance is contained within the capsule. The capsule ruptures between the dart body and the animal upon impact to thereby disperse said marking substance upon the animal about the area of the impact.

13 Claims, 3 Drawing Sheets

(56) References Cited

U.S. PATENT DOCUMENTS

2003/0194418 A1\* 10/2003 Hilton .................. A61K 9/0017
　　　　　　　　　　　　　　　　　　　　　　424/408
2016/0015499 A1\* 1/2016 Scott ........................ F42B 7/08
　　　　　　　　　　　　　　　　　　　　　　604/130

\* cited by examiner

MARKER CAPSULE FOR DRUG DELIVERY DART

BACKGROUND OF THE INVENTION

Related Applications

None.

Field of the Invention

The present invention relates to drug delivery darts, sometimes referred to as tranquillizer darts or remote drug delivery devices. More particularly, the present invention relates to drug delivery darts having a marker capsule containing a marking substance useful for marking an animal's skin or fur as a dose of drugs is injected.

Description of the Related Art

It is often times necessary to administer drugs to wild and domesticated animals. Since approaching animals on a one-to-one basis can be problematic, time consuming, and expensive, certain technologies have been developed for remote drug delivery. Perhaps the most commonly known system is the use of a tranquillizer gun and tranquillizer darts to subdue a dangerous animal from a distance, so that certain necessary actions can be performed on or with the animal. However, there are many other applications for remote drug delivery to wild and domesticated animals. For example, livestock herds or game animals may need to be treated for illness or inoculated against disease, and so forth, as is known to those skilled in the art.

Drug delivery darts are 'fired' toward animals using dart guns, also referred to as a 'projectors', which are non-lethal arms that provide sufficient velocity for the dart to be aimed, travel accurately toward the animal, and impact with sufficient force to impale the animal's, skin and inject a drug through a cannula on the front of the dart. Projectors generally operate on a compressed gas, although explosive charges are also utilized.

Reference is directed to FIGS. 1 and 2, which are side view and perspective view drawings, respectively, of an exemplary prior art drug delivery dart 2. This embodiment of a drug delivery dart 2 includes a body 4, which is essentially a syringe, having a tailpiece 12 and a stabilizer 14. The stabilizer 14 may also include a tuft of fiber, fins, or feathers that act as flight stabilizers. The front of the body 4 is a ferrule 6, which couples to a cannula 8. The body 4 and cannula 8 form the essential syringe and hypodermic needle used to inject a drug. An internal plunger (not shown) inertially pushes the drugs out the cannula on impact. The ferrule adds front weight and strength to the dart 2. Along the cannula 8 is a conical collar 10, which may be made of gelatin, and serves to retain the dart in place after it impales the animal. This may also be referred to as the 'gelatin collar' 10. Although, the reliability of this action is somewhat marginal as it greatly depends on the nature of the animal tissue into which the cannula 8 penetrates. Also, the gelatin collar 10 may be replaced with a sort of barb in certain drug delivery darts. Modern darts are approximately one-half inch in diameter, although other calibers are known. The length of the dart may be adjusted to allow for greater or lesser volumes of drug delivery.

In the situation where several animals are to be treated with a drug, or in the case of a herd of animals or a number of wild animals within a habitat, it is important that each animal is injected with a single dose of drugs, but not plural doses. In the past, operators have relied upon the dart hanging from the animal for a period of time, by virtue of the aforementioned gelatin collar, to establish that each animal has had the requisite injection, and so as to avoid giving any animal a second injection. However, the reliability of retention of the dart in this manner is not high, and operators have given double doses, which may cause harm to the animals and will result in economic waste. Thus it can be appreciate that there is a need in the art to overcome these problems in the art.

SUMMARY OF THE INVENTION

The need in the art is addressed by the apparatus and methods of the present invention. An illustrative embodiment of the present disclosure teaches a marker capsule for use in conjunction with a drug delivery dart that is used to inject a drug into an animal upon impact therewith. The drug delivery dart has a dart body and a cannula extending therefrom. The marker capsule includes a capsule formed of a rupturable material that has a central aperture formed therethrough, and the aperture is sized for disposition about the drug delivery dart cannula. A marking substance is contained within the capsule, and, the capsule ruptures between the dart body and the animal upon impact to thereby disperse the marking substance upon the animal about the area of the impact.

In a specific embodiment of the foregoing marker capsule, the rupturable material is a membrane that has a tensile strength selected to rupture at impact velocities that are suitable to enable drug delivery by the drug delivery dart. In another specific embodiment, the rupturable material is gelatin that has been platicized to control tensile strength.

In a specific embodiment of the foregoing marker capsule, the marking substance is a non-toxic fluid mixed with a colored dye. In another specific embodiment, the marking substance includes a food-grade vegetable dye.

In a specific embodiment of the foregoing marker capsule, the capsule is formed as a geometric torus. In a refinement to this embodiment, the geometric torus has a circular cross section. In another refinement to this embodiment, the geometric torus has dee-shaped cross section with a straight portion along its circumference that is positioned along the aperture.

In a specific embodiment, foregoing marker capsule further includes a rigid cap having a cylindrical portion with plural ports formed therethrough, and an end cap with a central opening for clearing the cannula. The cap is positioned over the capsule upon the dart body. Upon impact, the cap slides over the dart body to crush the capsule and expel the marking substance through the plural ports.

The present disclosure also teaches a method of marking a animal when impacted by a drug delivery dart. The drug delivery dart has a dart body with a cannula extending therefrom, and functions together with a marker capsule formed of a rupturable material, which has a central aperture formed therethrough. The capsule is filled with a marking substance. The method includes the steps of engaging the capsule with the drug delivery dart by inserting the cannula through the aperture in the capsule, and, impacting the drug delivery dart against the animal such that the cannula pierces the animal. The impact results in rupturing of the capsule between the dart body and the animal to disperse the marking substance upon the animal about the area of impact.

In a specific embodiment of the foregoing method, the impacting step further includes the step of launching the drug delivery dart using a gas pressure driven projector.

The present disclosure also teaches a drug delivery dart with a marking feature that is used to inject a drug into an animal upon impact while leaving a visible mark to indicate that a drug dose has been injected. This includes a drug delivery dart having a dart body and a cannula extending therefrom, and, a capsule formed of a rupturable material, which has a central aperture formed therethrough, and where the aperture is positioned about the drug delivery dart cannula and adjacent to the dart body. A marking substance is contained within the capsule. The capsule ruptures between the dart body and the animal upon impact to disperse the marking substance upon the animal about the area of the impact.

In a specific embodiment of the foregoing dart, the marking substance is a non-toxic fluid mixed with a colored dye. In another specific embodiment, the capsule is formed as a geometric torus.

In a specific embodiment, the foregoing dart further includes a rigid cap having a cylindrical portion with plural ports formed therethrough, and an end cap with a central opening for clearing the cannula. The cap is disposed over the capsule upon the dart body, and, the cap slides over the dart body upon impact to crush the capsule and expel the marking substance through the plural ports.

DESCRIPTION OF THE INVENTION

Figure 1:
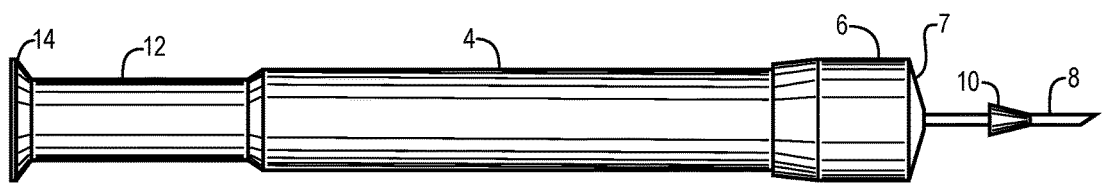
FIG. 1 is a side view drawing of a prior art drug delivery dart.

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components, and method steps, have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

The present disclosure teaches a marking capsule, an improved drug delivery dart, and a method of utilization thereof, which address the problems in the prior art. The marking capsule, which is filled with a marking material, is positioned at the front of a drug delivery dart. The capsule is formed of a rupturable material so that it bursts upon impact with an animal such that the marking substance is dispersed onto the skin or fur of the animal about the point of impact. This action leaves a clear indication that the animal has been given an injection. Both the rupturable material and the marking material are selected to be inert and non-harmful to the animal. Food grade components can be utilized, and may include vegetable dyes in suitably bright and contrasting colors. The capsule has a central aperture formed through it so that it may be slid over the cannula of a drug delivery dart and rest against the body of the dart, such as the ferrule in the aforementioned prior art darts. It is beneficial that the capsule be uniformly symmetrical about the cannula so that is does not significantly alter the balance and aerodynamic characteristics of the dart. A cap may be placed over the marker capsule to protect it and facilitate the balance and aerodynamic profile of the integrated components.

Figure 2:
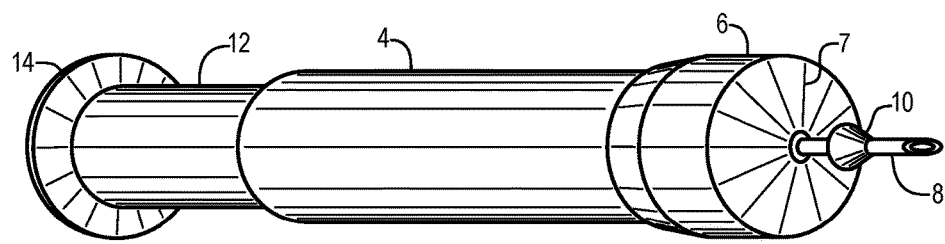
FIG. 2 is a perspective view drawing of a prior art drug delivery dart.

The rupturable material may be gelatin that is softened with a plasticizer, such as glycerin, propylene glycol, diethylene glycol, or hexanetriol. It is noteworthy that the flexibility of the capsule facilitates the capsule aperture's passage over the gelatin collar on the cannula of the dart, as discussed regarding FIGS. 1 and 2, above. However, the tensile strength of the capsule must yield to the force of impact so that the capsule busts and disperses the marking substance. Tensile strength can be controlled by the thickness of the capsule material, and thicknesses in the range of 0.010" to 0.030" are suitable. Although, other thicknesses may be utilized depending on the tensile strength of such material. Having stated this, it should be appreciated that the capsule material could be other organic or polymeric compounds with similar physical properties, but which are inert with respect to the animal biological systems and health.

Figure 3:
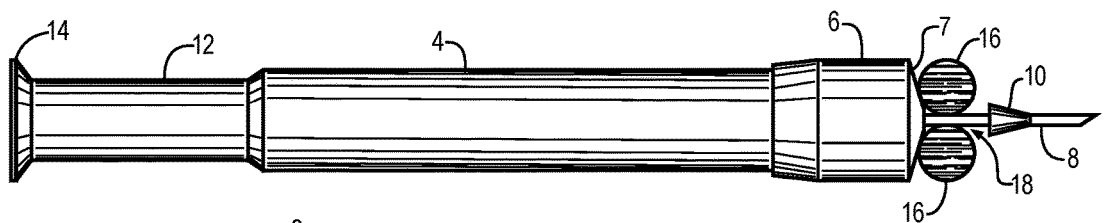
FIG. 3 is a side view drawing of a drug delivery dart with a marker capsule according to an illustrative embodiment of the present invention.
Figure 4:
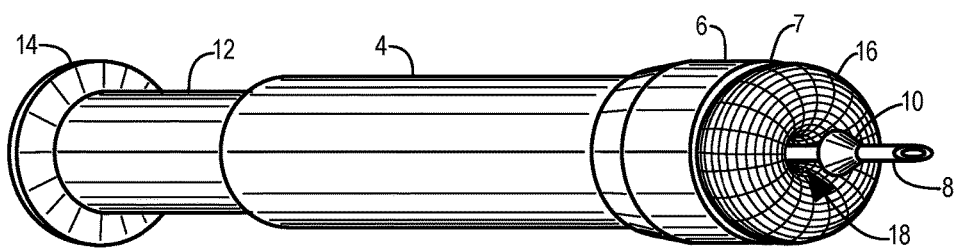
FIG. 4 is a perspective view drawing of a drug delivery dart with a marker capsule according to an illustrative embodiment of the present invention.

Reference is directed to FIG. 3 and FIG. 4, which are side view and perspective view drawings, respectively, of a drug delivery dart 2 with a marker capsule 16 according to an illustrative embodiment of the present invention. The drug delivery dart (hereinafter "dart") includes a body 4 with ferrule 6 at the front end thereof. A tailpiece 12 with stabilizer 14 are at the back end of the dart 2. A cannula 8 extends out the front of the ferrule 6, which functions as a hypodermic needle, injecting a drug (not shown) upon impact with the animal (not shown). The internal structure and functions of the dart 2 are known to those skilled in the art. The marker capsule 16 is a donut shape, meaning a geometric torus having a circular cross section, in this embodiment. The torus shape of the marker capsule 16 provides a central aperture 18, which provides clearance and a passageway for the cannula and gelatin collar 10 as the marker capsule 16 is slid over the cannula 8. Note that the pliability of the marker capsule 16 outer membrane material stretches to allows the gelatin collar 10 to pass through the aperture 18, and then relaxed to effectively retain the marker capsule on the cannula 8. The integrated dart 2 and marker capsule 16 are thusly ready to fire from a projector device (not shown). The dart 2 is loaded into a projector (not shown), aimed, and discharged in the direction of an animal (not shown) to thereby inject the requisite drug, while leaving a mark in the skin or fur of the animal.

Figure 5:
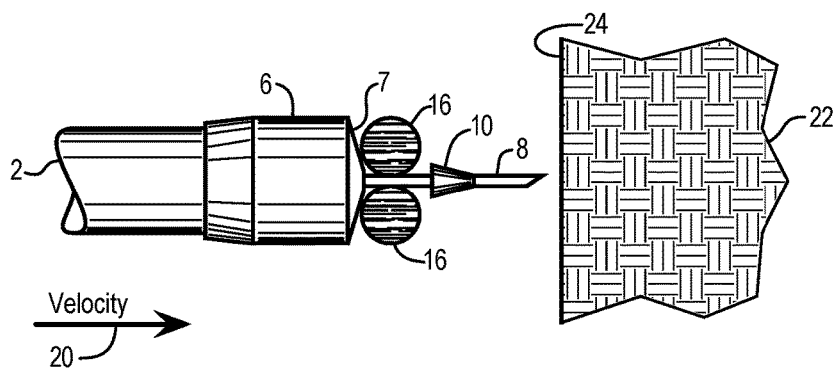
FIG. 5 is a side view drawing of a drug delivery dart with marker capsule engaging an object according to an illustrative embodiment of the present invention.

Reference is directed to FIGS. 5 through 8, which are side view drawings of a drug delivery dart 2 with marker capsule 16 engaging an object 22 according to an illustrative embodiment of the present invention. This sequence of drawings illustrates the process of injecting a drug and marking an object, which is typically an animal. In FIG. 5, a dart 2 is travelling at a suitable velocity 20 toward the exterior surface 24 of an object 22 prior to impact. The ferrule 6 of the dart 2 has a front surface 7, against which a marker capsule 16 is positioned. The cannula 8 of the dart 2 passes through an aperture in the marker capsule 16, and also includes a gelatin collar 10. The outer surface 24 of the object 22 will typically be the skin of an animal.

Figure 6:
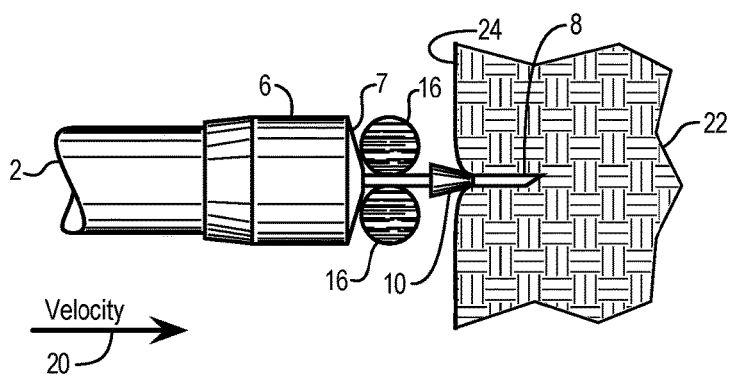
FIG. 6 is a side view drawing of a drug delivery dart with marker capsule engaging an object according to an illustrative embodiment of the present invention.
Figure 7:
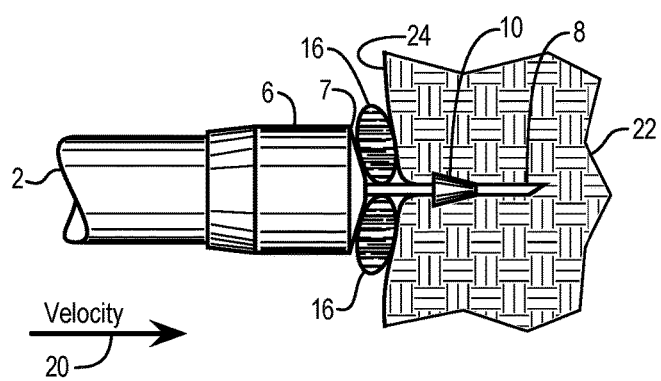
FIG. 7 is a side view drawing of a drug delivery dart with marker capsule engaging an object according to an illustrative embodiment of the present invention.
Figure 8:
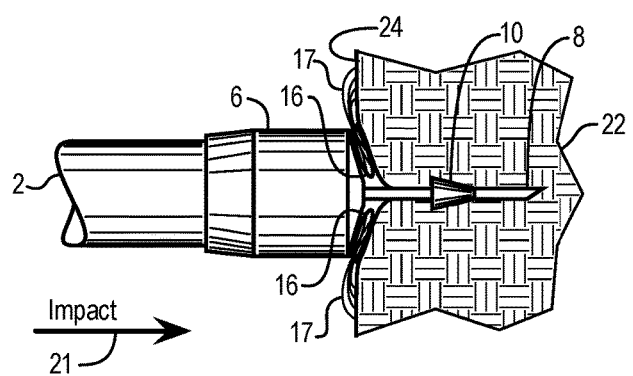
FIG. 8 is a side view drawing of a drug delivery dart with marker capsule engaging an object according to an illustrative embodiment of the present invention.

In FIG. 6, the cannula 8 of the dart 2 has pierced the skin 24 of the animal 22, and the gelatin collar 10 has just reached the skin 24, which is somewhat displaced as it is pierced. In FIG. 7, the cannula 8 and gelatin collar 10 have entered the animal 22 and the marker capsule 16 is being deformed between the animal 22 skin 24 and the front 7 of the dart's 2 ferrule 6. At this point the pressure of the marking substance in the marker capsule 16 has increased, but the forces have not yet exceeded the tensile strength of the marker capsule 16. In FIG. 8, the dart 2 has impacted 21 the skin 24 of the animal 22, and the drug (not shown) is being injected into the animal 22. The compressive forces acting on the marking substance in the marker capsule 16 have exceeded the tensile strength, which has ruptured the maker capsule 16, causing the marking substance 17 therein to disperse and mark the skin 24 in the area about the point of impact. Note that the impact 21 velocity and momentum cause the marking substance 17 to impinge in the skin of the animal 24, as opposed to dispersing outwardly to the local environment. Thusly, the animal 22 is injected with the drug and the skin 24 has been marked with the marking substance 17, indicating such actions have occurred.

Figure 9:
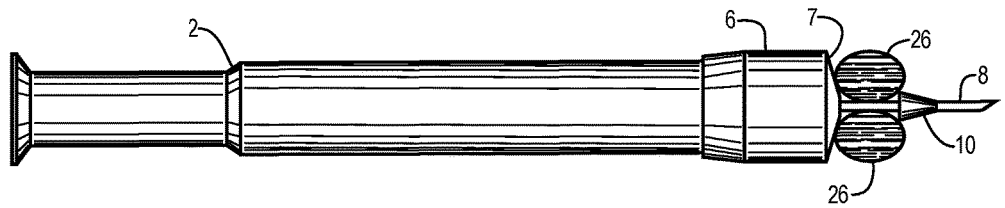
FIG. 9 is a side view drawing of a drug delivery dart with a marker capsule according to an illustrative embodiment of the present invention.

Reference is directed to FIG. 9, which is a side view drawing of a drug delivery dart 2 with a marker capsule 26 according to an illustrative embodiment of the present invention. Note that in the prior embodiment, the marker capsule was a torus with a circular cross section. The embodiment in FIG. 9 provides a marker capsule 26 that is also a torus, but which has an oval cross section, as illustrated. The benefit of this configuration is that a greater volume of marking substance can be contained in the capsule 26. Note also that the length of the capsule 26 along the length of the cannula 8 is greater, which places closer to the gelatin collar 10. The marker capsule still rests against the face 7 of the dart ferrule 6. Note also that the outside diameter of the marker capsule 26 is equal to, or less than, the outside diameter of the dart 2. This is so the marker capsule will pass through the bore of a projector.

Figure 10:
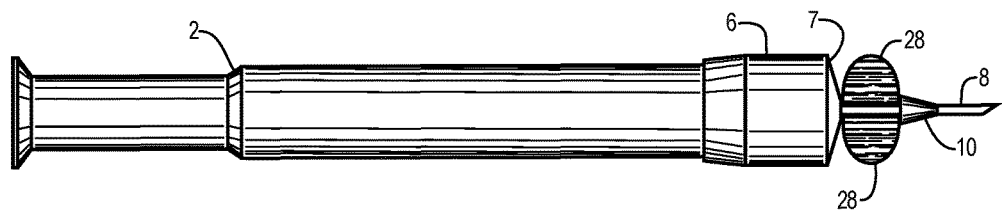
FIG. 10 is a side view drawing of a drug delivery dart with a marker capsule according to an illustrative embodiment of the present invention.

Reference is directed to FIG. 10, which is a side view drawing of a drug delivery dart 2 with a marker capsule 28 according to an illustrative embodiment of the present invention. This embodiment provides a marker capsule 28 that is also a torus, but which has a dee-shaped cross section, as illustrated. Note that he straight portion of the circumference lies along the length of the cannula. The benefit of this configuration is that an even greater volume of marking substance can be contained in the capsule 28. Note that the length of the capsule 28 along the length of the cannula 8 reaches to the back side of the gelatin collar 10. The marker capsule 28 still rests against the face 7 of the dart ferrule 6. Note also that the outside diameter of the marker capsule 28 is also equal to, or less than, the outside diameter of the dart 2.

Figure 11:
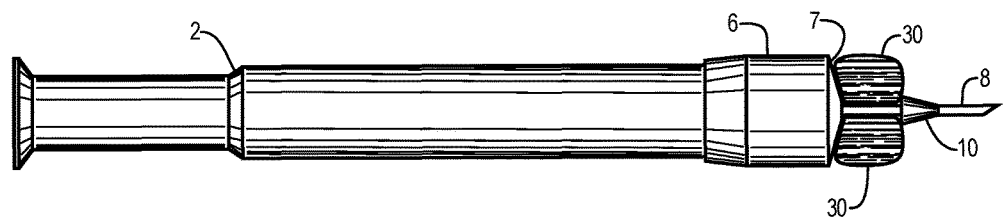
FIG. 11 is a side view drawing of a drug delivery dart with a marker capsule according to an illustrative embodiment of the present invention.

Reference is directed to FIG. 11, which is a side view drawing of a drug delivery dart with a marker capsule according to an illustrative embodiment of the present invention. This embodiment provides a marker capsule 30 that is also a torus, but which has a conformally shaped cross section, as illustrated. This embodiment illustrates the concept of forming the marker capsule 30 to achieve the greatest possible volume while still fitting through the bore of a projector.

Figure 12:
FIG. 12 is a side view drawing of a drug delivery dart with a marker capsule and protective cap according to an illustrative embodiment of the present invention.

Reference is directed to FIG. 12, which is a side view drawing of a drug delivery dart 32 with a marker capsule 38 and protective cap 40 according to an illustrative embodiment of the present invention. In this embodiment, the marker capsule 38 is a torus with circular cross section, as illustrated. The marker capsule 38 is disposed about the cannula 42 behind a gelatin collar 44, and against the forward face of the ferrule 34. Note that the ferrule 34 has a reduced diameter portion 36, which accommodates the thickness of the cap 40, so as to maintain the outside diameter within the constraints of the projector bore (not shown) diameter. On impact, the cap 40 is driven toward the front face of the dart, and slides over the outside diameter of the ferrule's 34 reduced diameter portion 36. Thusly, the marker capsule is crushed and ruptures between the front face of the ferrule 34 and the inside of the cap 40.

Figure 13:
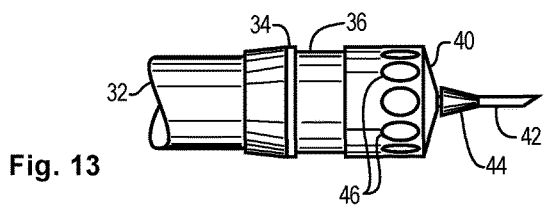
FIG. 13 is a partial side view drawing of a drug delivery dart with a marker capsule and protective cap according to an illustrative embodiment of the present invention.

Reference is directed to FIG. 13, which is a partial side view drawing of a drug delivery dart 32 with a marker capsule (not shown) and protective cap 40 according to an illustrative embodiment of the present invention. FIG. 13 corresponds to FIG. 12, but illustrated the outer surface of the cap 40. In particular, note that there are plural ports 46 formed through the side of the cap 40, which enable the marking substance (not shown) to be expelled upon crushing and rupture of the marker capsule (not shown) and disperse onto the animal that is impacted by the dart 32.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A marker capsule for use in conjunction with a drug delivery dart used to inject a drug into an animal upon impact therewith, the drug delivery dart having a dart body and a cannula extending therefrom with a collar disposed about the cannula that serves to retain the dart in place after it impacts the animal, the marker capsule comprising:
    a capsule formed of a rupturable and flexible material, and having a central aperture formed therethrough, said aperture sized for disposition about the drug delivery dart cannula, and wherein said flexible material stretches to allow the collar on the cannula to pass therethrough and further relaxes to effectively retain said capsule on the cannula between the dart body and the collar;
    a marking substance contained within said capsule, and wherein
    said capsule ruptures between the dart body and the animal upon impact to thereby disperse said marking substance upon the animal about the area of the impact.

2. The marker capsule of claim 1, and wherein:
    said rupturable material is a membrane having a tensile strength selected to rupture at impact velocities that are suitable to enable drug delivery by the drug delivery dart.

3. The marker capsule of claim 1, and wherein:
    said rupturable material is gelatin that has been plasticized to control tensile strength.

4. The marker capsule of claim 1, and wherein:
    said marking substance is a non-toxic fluid mixed with a colored dye.

5. The marker capsule of claim 1, and wherein
    said marking substance comprises a food-grade vegetable dye.

6. The marker capsule of claim 1, and wherein:
    said capsule is formed as a geometric torus.

7. The marker capsule of claim 6, and wherein:
    said geometric torus has a circular cross section.

8. The marker capsule of claim 6, and wherein:
    said geometric torus has dee-shaped cross section having a straight portion along its circumference that is disposed along said aperture.

9. A method of marking an animal when impacted by a drug delivery dart that has a dart body and a cannula extending therefrom with a collar disposed about the cannula that serves to retain the dart in place after it impacts the animal, using a marker capsule formed of a rupturable and flexible material, and having a central aperture formed therethrough, the capsule filled with a marking substance, the method comprising the steps of:
    engaging the capsule with the drug delivery dart by inserting the cannula through the aperture in the capsule, thereby stretching the flexible material as the collar passes through the aperture, and wherein the flexible material relaxes, thereby effectively retaining said capsule on the cannula between the dart body and the collar;
    impacting the drug delivery dart against the animal such that the cannula pierces the animal, and thereby
    rupturing the capsule between the dart body and the animal upon impact to disperse the marking substance upon the animal about the area of impact.

10. The method of claim 9, and wherein:
    said impacting step further comprises the step of launching the drug delivery dart using a gas pressure driven projector.

11. A drug delivery dart with a marking feature that is used to inject a drug into an animal upon impact therewith while leaving a visible mark to indicate that a drug dose has been injected, comprising:
    a drug delivery dart having a dart body and a cannula extending therefrom with a collar disposed about said cannula that serves to retain the dart in place after it impacts the animal;
    a capsule formed of a rupturable and flexible material, and having a central aperture formed therethrough, said aperture disposed about the drug delivery dart cannula, and wherein said flexible material stretches to allow the collar on the cannula to pass therethrough and further relax to effectively retain said capsule on the cannula between the dart body and the collar;
    a marking substance contained within said capsule, and wherein
    said capsule ruptures between said dart body and the animal upon impact to thereby disperse said marking substance upon the animal about the area of the impact.

12. The drug delivery dart of claim 11, and wherein:
    said marking substance is a non-toxic fluid mixed with a colored dye.

13. The drug delivery dart of claim 11, and wherein:
    said capsule is formed as a geometric torus.

* * * * *